United States Patent [19]

Obermayer et al.

[11] 4,356,969

[45] Nov. 2, 1982

[54] VAPOR DISPENSER AND METHOD OF MAKING SAME

[75] Inventors: Arthur S. Obermayer, Newton; Larry D. Nichols, Arlington, both of Mass.

[73] Assignee: Moleculon Research Corporation, Cambridge, Mass.

[21] Appl. No.: 737,324

[22] Filed: Nov. 1, 1976

[51] Int. Cl.³ ............................................. A61L 9/04
[52] U.S. Cl. .................................... 239/6; 239/56; 239/60
[58] Field of Search ............... 239/34, 35, 44, 51.5, 239/53–60, 6; 260/230

[56] References Cited

U.S. PATENT DOCUMENTS

| | | | |
|---|---|---|---|
| 1,478,208 | 12/1923 | Duddleson et al. | 239/55 |
| 1,826,115 | 10/1931 | Ziebarth | 239/35 |
| 2,572,669 | 10/1951 | Sarge et al. | 239/60 X |
| 2,626,833 | 1/1953 | Valentine | 239/56 |
| 3,770,199 | 11/1973 | Hoek et al. | 239/54 |
| 3,815,828 | 6/1974 | Engel | 239/56 |
| 3,844,478 | 10/1974 | Davis | 239/57 |
| 3,846,404 | 11/1974 | Nichols | 260/230 |
| 3,858,807 | 1/1975 | Rabussier et al. | 239/56 |
| 3,954,964 | 5/1976 | Kuderna, Jr. | 239/60 X |
| 3,985,298 | 10/1976 | Nichols | 239/54 |
| 3,990,848 | 11/1976 | Corris | 239/57 X |
| 4,051,628 | 10/1977 | Knapp et al. | 239/35 |

Primary Examiner—Robert W. Salfer
Attorney, Agent, or Firm—Richard P. Crowley

[57] ABSTRACT

A vapor dispenser which comprises a reservoir to contain a nonflowing liquid whose vapor is to be dispensed into the environment and an outer covering about the reservoir which includes a membrane vapor-emitting surface through which the vapor is dispensed from the reservoir to the environment.

29 Claims, 4 Drawing Figures

VAPOR DISPENSER AND METHOD OF MAKING SAME

BACKGROUND OF THE INVENTION

Vapor-dispensing systems are employed to dispense vapors into a particular environment and include both passive systems, whereby the vapor is dispensed by stagnant diffusion and/or random air circulation over the surface of a vapor dispenser, and active systems which involve a forced air flow over the dispenser. Vapor dispensers may be employed for dispensing a variety of vapors into an environment, including medicinal vapors, odor counteractants, pheromones, insect repellents, pesticides, and perservatives, but more particularly are directed to air-freshening dispensers and systems wherein a volatile fragrance is vaporized from the dispenser into the environment over a desired period of time with a desired threshold or intensity level.

Standard air-freshener delivery dispensers and systems presently include such static-type systems as cans of a liquid to be dispensed which include a wick as a dispensing surface, aqueous gels containing an active-fragrance ingredient, and sponges, waxes, blotting papers and the like containing or treated with a fragrance. Active systems include dispenser-type containers wherein a vehicle-containing fragrance, either in gel, liquid or other form, is dispensed into the atmosphere by passing air over the fragrance-dispensing surface of the vehicle by the use of a battery- or power-driven fan.

Present commercial vapor-dispensing products and systems are not wholly satisfactory in that they include one or more disadvantages, such as being inconvenient for incorporation into the dispensing systems; providing nonuniform or uncontrolled release; being bulky or heavy; using a highly dilute fragrance-emission vehicle; holding only a very limited fragrance payload based on their size or weight; needing to be manually altered during use to obtain a near uniform fragrance release; retaining at the end of their effective or desired lifetime a large portion of the volatile fragrance within their structure; unstorable for extended periods of time without redistribution of the fragrance or other internal liquid; leaking when the vapor-dispensing package is damaged, shaken, inverted or unsatisfactorily packaged; being uneconomical for manufacture and distribution; and having an undesirably short or long lifetime.

It is, therefore, desirable to provide a simple, economical, easily manufactured, controlled-release vapor-dispenser produce and method of preparing the same, which will overcome one or more of the disadvantages of the present commercial vapor-dispenser products. It is recognized that it is a part of the prior art to load a volatile fragrance into a porous material, such as felt, blotting paper, sponge, etc., to provide a surface for the emission of vapor into the environment; that is, as a space air-freshener product. However, such products are not wholly satisfactory in use or performance, since there is poor or no control of the release rate of the fragrance over the desired time release span. In addition, attempts to incorporate a high volumetric amount of the liquid into the porous material often create leakage and drainage problems which are unsightly and often damage contiguous surfaces. Therefore, such products typically have an unsatisfactory performance life and/or nonuniform and unsatisfactory performance properties.

SUMMARY OF THE INVENTION

Our invention relates to a dispenser for the release of vapors into an environment and to the method of preparing and using such a dispenser. In particular, our invention relates to improved, controlled-release vapor dispensers which may be employed in both active and passive systems for the release of a fragrance or other volatile material into the atmosphere, and to a method of preparing such improved dispensers. More particularly, our invention concerns a simple, inexpensive, easily manufactured room or space air-freshener-dispenser product for dispensing a fragrance over a desired period of time into an environment, and to a method of preparing and using such product.

Our vapor dispenser comprises in combination: a reservoir containing a volatile liquid contained within a nonaqueous gel-like or porous material; and a contiguous vapor-permeable, surface-membrane material which covers at least a portion of the reservoir to define a vapor-emitting surface to the dispenser, thereby permitting a volatile material in the reservoir to be released at a controlled rate into the environment through the surface-membrane material. Optionally the vapor dispenser may include a nonvapor-permeable sheet or film material, which may be made of a rigid material to provide support for the dispenser, and wherein the membrane material may be secured by adhesives or by heat-sealing to the surface of the nonpermeable material, which typically is composed of a thermoplastic plastic sheet material. Optionally, also, the vapor-emitting surface may be covered by an outer, gross, porous sheath material to protect the vapor-emitting surface and/or to reduce convection in the boundary layer above the emitting surface, and preferably which is also heat-sealed or otherwise secured to the rest of the vapor dispenser.

Our vapor dispensers, such as air-freshener dispensers which contain a volatile fragrance, provide a number of advantages by employing the high-capacity, drainage-proof concept in combination with a contiguous, thin, surface-membrane, vapor-emitting material. Our vapor dispensers permit the employment and use of a high proportion of a fragrance or of a volatile material to be dispensed, can be conveniently incorporated and used in both active and passive vapor-dispensing systems, allow evaporation of the volatile material over an extended surface without nonuniform depletion of that surface (which would affect the controlled rate of release and intensity of the volatile material), allow control of the vaporization rate by limiting the surface area covered by the membrane material, allow control of use lifetime by the capacity of the reservoir, can be economically and easily manufactured in simple form, and further will not leak when damaged during manufacture, storage or use.

In general, for any particular volatile liquid, the larger the vapor-permeable membrane surface area, the more rapid the rate of release of volatile liquid from the vapor dispenser. Thus, the rate of release and the resulting local vapor concentration can be controlled by the choice of the amount of vapor-permeable area exposed. In order to increase the lifetime of duration of emission from a vapor dispenser designed with a particular membrane surface area for a particular desired intensity, it is necessary to increase the capacity of the reservoir to allow the use of larger quantities of volatile liquid. A particular advantage of our vapor dispenser is that essentially all; for example 90%, of the volatile liquid can be vaporized without altering the concentrations of each component in the liquid composition in both the membrane and the reservoir.

The reservoir employed in our vapor dispenser may comprise in one embodiment a nonflowing, nonaqueous gel whose major component comprises the volatile material to be dispensed, or a liquid or a mixture of materials which include that volatile material, such as a fragrance. Such nonaqueous gels may be formed by the addition of various gelling agents, such as waxes and other natural or synthetic polymeric materials, which can convert a liquid, such as an organic liquid, into a nonaqueous gel or gel-like form. Suitable nonaqueous gels would include, but not be limited to those gels containing a fragrance which are non-flowing during normal use and handling, but can be so constituted so as to flow under applied pressure, so that the gel may be injected or otherwise placed in the reservoir during the manufacture, but which prevent any leakage from occurring in the event that a potential leak occurs in the vapor-dispensing product. Such thixotropic gels containing, for example, a volatile fragrance to be employed in an air-freshener dispenser, may be formed in a nonaqueous system, for example, by the use of additive amounts of a gelling agent, such as less than 10% of carnauba wax in an essential oil, or other gelling-type materials. Such gel fragrances are easy to handle during manufacture, avoid potential leakage and simplify manufacturing, and yet such gels retain high levels of fragrance loading, so that they may be easily and advantageously employed as a reservoir in our vapor dispensers.

In another embodiment, our reservoir may comprise an inert, insoluble, highly porous, fibrous or cellular material capable of holding a high capacity of liquid, ranging from a typical minimum of about twice the dry weight of the reservoir material to about, for example, five to ten times the dry weight of the reservoir material. Such material can comprise woven or nonwoven natural or synthetic fabrics or fibers (e.g., propylene, polyesters) or a combination thereof, as well as cellular open-cell foams, and would include such specific materials as natural or synthetic felts or fabrics, paper like blotting paper, and urethane open-cell foams. It is most desirable that the porous material be capable of holding at least several inches of height of the liquid; e.g., over 3 inches, such as, for example, the liquid fragrance to be employed, in the reservoir without dripping, leaking, or other drainage of the liquid material, in the event the surface-membrane emittor or any other portion of the dispenser is punctured or improperly sealed. Typically and in addition, such porous materials should be inert to and insoluble in the volatile material to be dispensed into the environment, and should be inexpensive. The purpose of the reservoir, whether of the gel or porous material form, is to provide high capacity, and a controlled, low-cost source of volatile materials to be emitted into the environment through the surface-membrane emittor. In typical room air-freshener dispensers, for example, the thickness of our reservoir, either a gel or porous material, would generally range from about 25 to 250 mils, but more particularly from about 50 to 150 mils.

In our dispenser, the reservoir is confined at least partially and used in combination with an overlay membrane sheet material whose purpose is to provide confinement of the volatile material to be dispensed, further preclude drainage of the liquid material from the gel or porous material reservoir, minimize transfer from the surface of the reservoir to the user's hand, and provide a visually attractive appearance, as well as to provide a relatively uniform and nonchanging vapor-emitting surface for the fragrance or other volatile material to be emitted into the environment.

A critical aspect of the overlay membrane sheet is its ability to absorb preferentially the volatile liquid from the reservoir, because of the lower bulk free energy resulting from the greater interfacial surface area for contact between the liquid and polymer matrix. The membrane surface overcomes the disadvantages associated with the use of a porous reservoir material alone, such as a porous blotting paper which has been saturated with a fragrance, and wherein, as the fragrance evaporates, there is a receding surface of liquid within the blotting paper and a resultant reduction in release rate. Thus, we have found that, by combining a porous surface-overlay-membrane sheet with a reservoir, the exposed outer surface of the membrane sheet is continually wetted with a volatile material, such as a fragrance, from the reservoir, and, therefore, provides an aid to uniformity in the release of the volatile material to the atmosphere over the desired period of time, which, for a typical air-freshener product, might vary from about 10 to 90 days.

The overlay sheet material may be composed of a single sheet material or of a number of sheets secured together as a composite, but typically should be such as to permit the sheet material to be secured, as by adhesives or heat-sealing, either to itself where the membrane surface forms the sole confining surface for the reservoir, or preferentially, as hereinafter described, to a vapor-nonpermeable backing sheet. The porous reservoir material can be separate from the overlay membrane material, or alternatively the overlay membrane can be formed as a coating on the porous reservoir material so that it is in fact an integral part of the reservoir material. The membrane surface should be thin; for example, not over 50 mils in thickness, for example, about 5 to 50 mils in thickness, and inert to and insoluble in volatile material to be dispersed. The membrane may be comprised of a porous single or multiple-layer pure or composite material.

The overlay sheet material should also be porous, with the pores being sufficiently smaller than those of the reservoir to allow it to draw volatile liquid from the gel or porous reservoir during evaporation. Thus, the thin overlay surface-membrane material should be capable of surrounding and confining at least part of one surface of the reservoir so as to define a vapor-emitting surface, and the overlay membrane sheet material is characterized by a porous structure, the porosity of which is finer than that of the reservoir material, so that the surface material will remain saturated with the volatile liquid, because the liquid in the reservoir is continuously drawn into the membrane to replace the liquid which has volatilized from the vapor-emitting surface.

The surface overlay sheet material of our vapor dispenser may comprise a wide variety of thin porous sheet materials, either alone or in combination, such as by lamination. Preferentially, overlay sheet material compositions with very small pores; for example, from $10^{-3}$ microns to $10^{-1}$ microns diameter, should be used. Larger pores; for example, from $10^{-1}$ to 10 microns, can be used but are not preferred, because they may lead to some leakage of liquid through the overlay sheet. The pores must be open-celled or interconnecting and allow for sufficient liquid mobility so that the front surface of the overlay sheet does not dry out, but is replenished by liquid transport from the rear surface of the overlay sheet. The chemical composition of the overlay sheet is restricted to materials, such as polymers, that do not dissolve or react with the liquid component and on which the liquid component has a positive spreading coefficient. For example, for organic liquid fragrance, the overlay sheet material should be made from an organophilic polymer, such as cellulose triacetate, polyethylene, polypropylene, polyester, or polyacrylates, and similar materials.

The overlay sheet material should have well defined pores, preferably with a high liquid content; e.g., of 70% or more by volume. Alternatively, chemically; etched, radiation-treated polymer materials, e.g. Nucleopore, or mechanically formed, porous polypropylene, e.g. Celgard, a trademark of Celanese Corp., or other porous materials, capable of holding a lower liquid content, can be used as the overlay sheet material. However, nonporous thermoplastics, where the liquid acts as a plasticizer for the polymer, will not generally function in the proper manner, because of the slow diffusion of the liquid through the overlay sheet material and because of specific chemical and physical interactions and solvating effects between different components of the liquid and polymer. A particular disadvantage of the use of plasticized polymers as an overlay material is that each chemical component in a liquid plasticized system diffuses at its own rate through the material, depending on its own molecular size and the solvating power. Thus, liquid will perform in a rather unpredictable manner as it diffuses through the plastic, and when multicomponent liquids are used; for example fragrances, there will be drift in the quality of the fragrance, because of the different components and their differing resulting rates of volatilization.

A dye or combination of dyes may be added to the liquid in the vapor dispenser so that a color change, either in color intensity or change in color, occurs as the liquid content of the vapor dispenser is depleted by evaporation. In order to obtain a color change, the dye must either have limited solubility in the liquid remaining after most of the volatile liquid has evaporated, or it must be preferentially absorbed by the residual solid in the reservoir or the overlay sheet. As the liquid volatilizes from the overlay sheet, the dye migrates within the vapor dispenser and concentrates in the regions of greatest compatability or precipitates out of solution after the saturation level has been exceeded. Thus, as the liquid vaporizes, the coloration of the overlay sheet changes; for example, it may decrease to the point in intensity where essentially no or little color is visible when 90% of the liquid has vaporized and the overlay sheet appears substantially white or as the original color. This color change upon evaporation acts as a lifetime indicator and makes the user aware that the vapor dispenser is depleted. In the preferred embodiment, a polymer-liquid composite material is used in the overlay sheet because of its optical transparency, high liquid-holding capacity, and its ability to shrink as the liquid evaporates and the material dries. One example of a change in color is the transformations, after 90% of volatilization, of a mixture of 0.06% Pylakrome Medium Green dye and 0.025% Sandoz Nitrofast Green dye from green to an apparent white in a cellulose triacetate polymer-liquid composite material bonded to a porous polyethylene sheet as the membrane material, with the reservoir containing a mint fragrance. When this same green dye solution and fragrance are used in a vapor dispenser with only the porous polyethylene sheet as the overlay sheet and a woven cotton fabric as the reservoir, the reservoir material becomes white and the overlay sheet retains the green dye color when the fragrance has evaporated. Another example is the color conversion of a fluorescein dye from fluorescent yellow to orange in a Poroplastic sheet containing propylene glycol when the glycol has evaporated. Alternatively, the color change can be achieved by a change in acidity, basicity or solvent character of the liquid as the more volatile components of the liquid evaporate and the change in the composition effects a color change in an indicating dye.

The vapor dispenser described herein may optionally be covered with a gross, porous, sheath material which, in addition to protecting and decorating the vapor-emitting surface, alters the rate and composition of the vapor released to the environment. The gross porous sheath reduces convection currents near the membrane vapor-emittor surface, so that diffusion processes become more significant and there is an increase in the thickness of the boundary layer which influences the volatilization rate and the liquid/vapor component composition, as in a liquid distillation or fractionation column. The gross porous sheath should be of such a thickness and quality as to retard vapor transfer through it, if such changes in rate and composition are desired. The qualities required are similar to those for good thermal insulation. Thus, porous sheets or fabrics of wool, nylon, polyester, cotton, polyurethanes, polyolefins, cellulosics or paper are generally acceptable for this purpose; although materials of finer porosity than the reservoir should be avoided to avert undesirable wicking action if the layers are in direct contact, increased release rates, and overly easy transfer of liquid to fingers or other surfaces. The effectiveness of a gross, porous sheath depends not only on the quality and thickness of the sheath material, but also on the magnitude of the convective currents outside of the sheath.

In one particularly preferred embodiment, the overlay sheet material comprises a film of a polymer-liquid composite (PLC) material wherein the liquid composes at least 70% of the PLC material, which material is described in U.S. Pat. No. 3,846,404, issued Nov. 5, 1974, hereby incorporated by reference in its entirety. The employment of a liquid-containing, polymeric, thin-film material, particularly a film material comprising a substance to be released into the atmosphere and within a cellulosic polymer, such as a cellulose triacetate containing from about 70 to 95% of a liquid material, is particularly advantageous in providing a uniform and controlled rate of release of the liquid loading in the polymer to the atmosphere. Such film material so prepared and as described has a series of interconnecting internal pores as large as a few hundred Angstroms; for example, 250 Angstroms, or as small as a few Angstroms; for example, 5 Angstroms. The cellulosic-type film may be prepared with a variety of pore sizes, and such polymer-liquid composite materials readily exchange their internal liquids for other miscible liquids or solutions. The liquid material contained in the PLC overlay film used in our vapor-dispenser material may comprise preferably the same liquid containing the same material as in the reservoir, or if desired may be of a different liquid initially, but, if the liquid in the reservoir is miscible with the liquid in the composite liquid-film material, then a diffusive exchange will take place. The thin composite liquid material permits a diffusive permeation of the liquid from the gel-like or porous reservoir throughout the material, and permits a controlled diffusion and the release of the volatile components of the reservoir into the atmosphere. Typically such materials are composed of cellulosic materials, such as cellulosic triacetate as the preferred material.

The preferred embodiment membrane material is prepared on a thin, porous, thermoplastic base material, either of woven of nonwoven thermoplastic fibers, such as, for example, wherein the liquid composite material is prepared on and secured to a porous nonwoven fabric-like sheet material composed of polyethylene, polypropylene or other thermoplastic materials, or the like. The base material may then be employed to heat-seal the composite overlay material, either to itself or preferably to a backing sheet. A particularly preferred base support material is Tyvek (a trademark of E. I. duPont de Nemours & Co.), a porous polyethylene nonwoven fabric sheet, which permits the PLC material to penetrate into the pores and to form a bonded composite thin membrane film particularly suitable for use in our vapor dispenser. PLC film alone, known as Poroplastic ® (a trademark of Moleculon Research Corporation), is not heat-sealable and is difficult to seal with adhesives. Therefore, the preparation of PLC material on a heat-sealable or adhesive-sealable or other sealable base material provides a convenient means for securing PLC material to other substrates in our dispenser. The preparation of the membrane as a composite material on a porous base material provides a significant improvement in the process for making PLC material, since curing times are greatly shortened because of liquid diffusion from both sides of the sheet, rather than only one side, which occurs with a typical nonporous web on which the polymer solution of the PLC is cast.

The employment of a polymeric liquid composite material as a controlled release material is described more particularly in U.S. Pat. No. 3,985,298, issued Oct. 12, 1976, hereby incorporated by reference in its entirety. This patent describes various volatile-like materials which may be incorporated into the liquid phase of the polymeric liquid composite material of the film. Although the PLC material alone is satisfactory for the controlled release of volatiles such as fragrances, it may be too expensive or impractical when a large quantity of fragrance; for example, 1 to 50 grams, is to be volatilized over a long period of time; for example, 7 to 90 days. However, the employment of such a composite material in combination with a distinct reservoir permits thin films of the material to be employed solely as a membrane, while the reservoir serves as a contiguous source of the liquid to be dispensed.

Any volatile material which is desired to be dispensed into the atmosphere may be employed alone or in combination, and would include essential oils, pesticides, medicinal materials and other materials. The use of the composite membrane material in combination with the reservoir also allows for easier processing, because the volatile liquid can be placed in the reservoir as the last step in vapor-dispenser fabrication; for example, by insertion of liquid through a hypodermic needle into the fibrous or cellular porous reservoir material or by extrusion of a gel into the space behind the overlay sheet. Normally employed for room air fresheners are those volatile fragrances containing various mixtures of essential oils and the like, such as mint, floral, lemon-lime and other fragrances. Before or after saturation of the porous reservoir or introduction of the gel-like material, the reservoir is enclosed within the surface-membrane sheet material, either with or without a backing, such as by sealing the membrane-surface material about its peripheral edges, and any final saturation or gel-loading is performed. The material is then suitable for passive use in room air or for active use in a dispenser where air is passed over the emittor surface of the membrane.

Our vapor dispenser material may be employed in a variety of forms, depending upon the requirements of the particular system; for example, it may be employed in flat, bent, toroidal, helical or spiral coil forms, with forced-air-type dispensers for use in active systems, wherein air from a driven fan is forced over the membrane-emittor surface, or it may be used in a passive system in a flat or attractively curved sheet form, whereby the vapor dispenser is placed in a stand or container, or is secured by a hook or adhesive to a surface, with one or more surfaces exposed, so that, by diffusion and circulation, the volatile material, such as a fragrance, is dispensed into a particular environment, such as a room, inside of a transportation vehicle or within another target environment.

Our vapor dispenser and its method of preparation and use will be described in its preferred embodiment in use as a passive room air freshener, and its preferred structural embodiment. However, it is recognized and is a part of our invention that various changes and modifications may be made in our vapor dispenser, as described and illustrated within the spirit and scope of our invention. Our invention will be described for the purpose of illustration only in connection with its structure and use as a room air freshener wherein the volatile material is a fragrant material.

DESCRIPTION OF THE EMBODIMENTS

Figure 1:
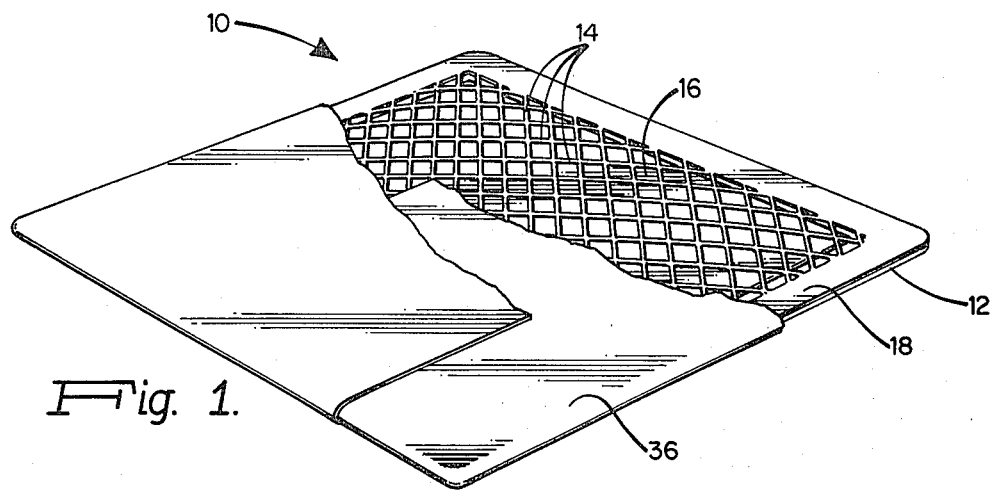
FIG. 1 is an illustrative perspective view of our vapor dispenser.
Figure 2:
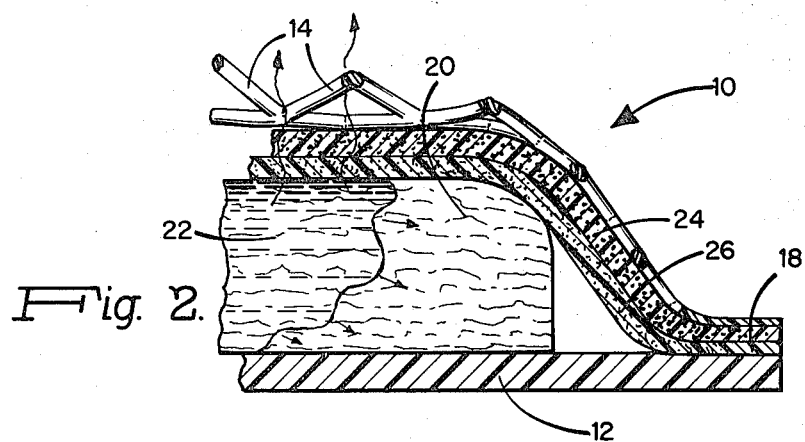
FIG. 2 is an enlarged fragmentary cross-sectional view of the vapor dispenser of FIG. 1.

FIGS. 1 and 2 show our vapor dispenser invention in the form of a passive, flat sheet, room air freshener, wherein the vapor dispenser 10 comprises a rigid, non-permeable, backing sheet 12 composed of a solid thermoplastic, such as polyethylene or polypropylene, which imparts rigidity to the vapor dispenser 10, so that it may be positioned for use as a passive device. Vapor dispenser 10 also includes a plastic net-like retaining material 14, the function of which material is to minimize inadvertent transfer of fragrance from the emitting surface of the dispenser to the hands of the user, and to provide a cosmetic effect for the overall appearance of the dispenser, and likewise to provide protection in case of accidental damage to the vapor-emittor surface and optionally to retard or otherwise modify release rates. A composite covering sheet material 16 is composed of a polymer-liquid composite material 24, such as cellulose triacetate (Poroplastic) which contains 70% of a volatile liquid fragrance to be dispensed by the device bonded to a thin porous spun-bonded polyethylene sheet material 26 (such as Tyvek), which sheet material is heat-sealable, so that composite material 16, together with the net-like sheet 14, may be heat-sealed to the backing 12 to form a peripheral heat-sealed edge 18.

The sheet material 26 is bonded to the polymer-liquid composite material 24 by casting the solution of the polymer material onto the porous sheet material, and, thereafter, incorporating the fragrance into the composite sheet material through the technique as described in the aforesaid U.S. patents incorporated by reference, or by exchange with the fragrance-filled reservoir after assembly. Contained within the covering sheet material 16, which forms the vapor-permeable emitter surface and the backing sheet 12, is a reservoir composed of a porous fibrous material 20, particularly a melt-bonded polyethylene/polypropylene nonwoven material having a thickness of about 25 to 300 mils which has been saturated with a dyed volatile fragrance, such as a Cool Blue Mint-type fragrance 22, to be dispensed into the atmosphere. The volatile liquid fragrance material 22 comprises from about three to eight times the weight of the porous material 20 in the reservoir. The exposed emitting surface of room air freshener 10 ranges from about 1 to 20 square inches (for a product designed to last a period of from, say, one week to 90 days). As illustrated in FIGS. 1 and 2, our vapor dispenser device is suitable for use as a room air freshener and permits the passage of volatile material 22 from the reservoir 20 through the thin porous heat-sealable sheet 26 to the layer 24, which surface is protected by the netting 14, and thus permits the vapor to be released continuously at a controlled rate to the atmosphere from the reservoir.

Figure 3:
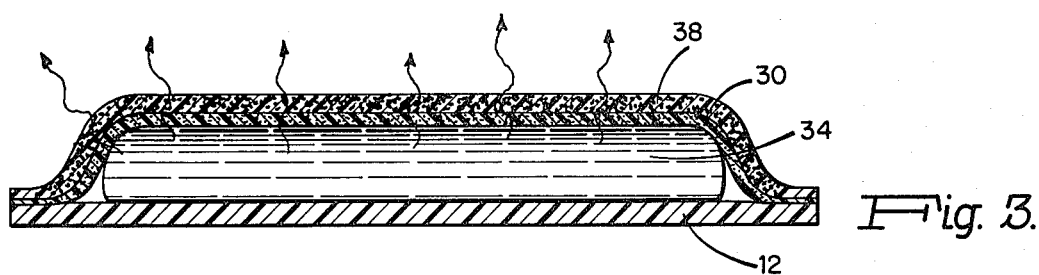
FIG. 3 is an illustrative representative cross-sectional view of another embodiment of our vapor dispenser.

FIG. 3 illustrates another embodiment wherein a rigid nonvapor-permeable backing sheet 12 is employed, with a reservoir comprising a gel-like material 34, the gel material composed essentially of a liquid in gel form which contains a volatile fragrance to be dispensed. The gel material is enclosed within a thin, porous, polymeric, membrane sheet material 30; for example, Celgard film, such as a sheet formed of polyethylene, having very fine pores therein; for example 200 to 400 Angstroms, and having a thickness of from, for example, 2 to 12 mils, the pores in the sheet being quite small to prevent leakage from the gel reservoir, so that the surface of the sheet material will serve as a vapor-emittor surface.

Over the vapor-emitter surface 30 is another macroporous sheath material 38, such as paper, open-cellular sponge or a porous woven or nonwoven polymeric fibrous material, in which the pores are of greater size than the pores of the underlying material 30, and whereby the sheet material 38 is employed to reduce the rate of evaporation of the fragrance from the reservoir 34. By the use of a macroporous sheath 38, we have found that the rate of evaporation from the reservoir can be reduced. This reduction in the rate of evaporation is useful to prevent too rapid an evaporation rate; for example, in a reservoir where a particularly volatile material is used. The porous material 38 also increases the thickness of the boundary layer above the vapor-emitter surface 30, and thereby also reduces the overall rate of release. The macroporous sheath 38, which may be comprised of wool, polyester, paper, fibers or the like, does not become wet with the volatile liquid contained within the reservoir 34, because the liquid passes from the liquid phase in the reservoir to a volatile gaseous phase upon leaving the vapor-emittor surface 30, and remains as a vapor as it diffuses through the macroporous sheath 38 out into the atmosphere. Thus, the liquid-containing product of our vapor dispenser having a macroporous surface, as illustrated in FIG. 3, has a surface which is dry to the touch of the user. This embodiment illustrates the employment of an overlay surface-membrane material which is not a liquid composite material, the employment of a gel-type material as a reservoir, and the use of a macroporous sheath to retard evaporation.

Figure 4:
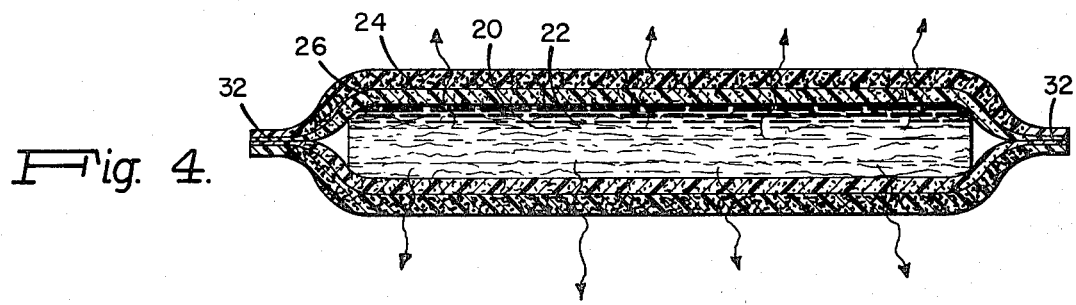
FIG. 4 is an illustrative representative cross-sectional view of a further embodiment of our vapor dispenser.

FIG. 4 is an illustration of another embodiment of our vapor dispenser, wherein the dispenser comprises two opposing emitting surfaces, and wherein the composite sheet material 16 of FIG. 1 is comprised of the Poroplastic polymer-liquid composite material 24 cast on and bonded to a heat-sealable plastic fibrous Tyvek sheet 26, and is employed to surround totally a porous material reservoir 20 containing a fragrance 22, and wherein the composite sheet material is sealed at the peripheral edge 32 to enclose the reservoir. In this particular form of vapor dispenser, arrows illustrate the flow of vapor emission from the surfaces. This form is illustrated in sheet form, but may be employed in coil form, particularly in an active system.

The composite heat-sealable material 16 employed as an overlay surface-membrane material is a unique product which comprises a polymer-liquid composite material secured to a heat-sealable substrate, which, in conjunction with a macroporous matrix 20 or 34 to serve as a reservoir, provides for a novel product suitable for use as a vapor dispenser. The composite sheet material 16 is prepared by coating or casting the polymer-liquid composite material on the substrate and impregnating with a particular material, such as a volatile fragrance or a variety of other active ingredients which are desired to be dispensed into the atmosphere. The composite film is thus rendered heat-sealable to another piece of similar film or a backing material, such as polyethylene, polypropylene and other plastics, aluminized Mylar or some other convenient material. In one embodiment, a PLC layer is cast or coated onto a relatively thin macroporous film subtrate which has no or relatively little holding capacity for the fragrance or liquid material of the PLC. The resulting composite can then be heat-sealed to a fragrant-impermeable backing, where an appropriate void for the inclusion of a reservoir is present. The employment of a macroporous sheath over the vapor-emitter surface of the composite liquid membrane, as described previously, is desirable when a reduction in the initial rate of release of the volatile material from the surface is warranted.

By our techniques and structures, the fragrance or active agent holding capacity of a vapor dispenser product utilizing PLC film is increased without increasing the required quantity of the PLC film. Since in general the substrate material; that is, the reservoir, is considerably less expensive than the fragrance- or liquid-containing PLC film so formed, a more economical product may be manufactured. In addition, the heat-sealable material on which the film is formed may act as a web during the continuous casting of the Poroplastic film, thereby permitting much more rapid continuous processing of the composite membrane film. As illustrated more particularly in FIGS. 1 and 2, the emitter surface is a PLC film which is of an ultramicroporous character, and which prevents the liquid in the lower heat-sealable porous layer and that present in the reservoir from dripping or leaking out through the Poroplastic film onto the surface, but permits the unique release properties of the PLC film to provide for controlled release. Thus, our invention, in its simplest form, comprises a composite PLC film containing a fragrance or other liquid material cast on and bonded to a more porous heat-sealable thermoplastic reservoir and support film material which is less expensive, and which contains therein a liquid which is saturated with the volatile fragrance, and having an impermeable backing sheet bonded in turn to the reservoir material.

EXAMPLE 1

The release characteristics of a PLC composite film which contained 150 mg/in$^2$ of a fragrance was tested in a standard, wall-type, forced-air-flow fragrance dispenser. It was found that the fragrance was released at 32 mg/in$^2$ per day and that the useful life of the product was therefore about 5 days. It was desired to achieve a release rate of 5 mg/in$^2$ per day, so that the product would have a useful life for 30 days.

Experiments were conducted by placing various thicknesses of paper over a piece of Poroplastic composite film which contained 150 mg/in$^2$ of the same fragrance. It was found that a 0.020-inch thick paper covering reduced the release rate to 11.4 mg/in$^2$ per day and would, therefore, produce a product with a useful life of about 13 days. A 0.040-inch thick paper covering led to a release rate of 6 mg/in$^2$ per day or a useful product life of 25 days. An 0.060-inch covering produced a release rate of 4.75 mg/in$^2$ per day or a useful product life of 31.6 days.

It was found that macroporous sheath over fragrance containing PLC composite film could effectively reduce the release rate of a highly volatile fragrance. In one experiment (Table I), five different PLC composite films were loaded with a volatile floral gardenia fragrance containing an average of 284 mg/in$^2$. Four of the samples were covered with various macroporous sheaths, while the control sample was without a sheath. The five samples were wall-mounted and allowed to perform without a fan; that is, as passive vapor dispensers. The results were as follows:

TABLE I

| Sample | Loss in mg/in$^2$/day | Product life in days |
|---|---|---|
| Control | 41.6 | 6.8 |
| 0.007 wool sheath | 26.5 | 10.7 |
| 0.004 polyester sheath | 25.8 | 11.0 |
| 0.0065 paper sheath | 27.9 | 10.2 |
| 0.0197 paper sheath | 22.3 | 12.7 |

Experiments conducted with different volatile liquids and with different types of macroporous sheath of various thicknesses affirmed the value of macroporous sheath as means for reducing the volatility of liquids from Poroplastic composite emitting surfaces. Thus, liquids which are too volatile for practical use (that is, evaporate too rapidly or in less time than the desired time) in PLC composites without a sheath can be made to perform as desired by using various macroporous sheaths in various thicknesses.

EXAMPLE 2

A sample of 0.20-inch thick blotter paper (Am. Pad & Paper 1968) having a dry density of 200 mg/in$^2$ was coated with a 0.005-inch thick layer of Poroplastic material. The paper/Poroplastic laminate was impregnated by standard procedures with an S5 Clean fragrance material. During the impregnation, the dry blotter swelled from 0.020 inch to 0.035 inch thick. The resultant laminate was 0.040 inch thick and contained 479 mg/in$^2$ of S5. The Poroplastic layer contained 75 mg/in$^2$ of S5, while the blotter contained 404 mg/in$^2$ of S5. The sample was then wrapped around the inner circumference of an active, forced-air-flow dispensing canister with only the Poroplastic composite surface exposed, and weight loss in mg per hour per in$^2$ was monitored for 25 hours in an accelerated tester with an airflow of 100 cfm. Weight loss was found to be 16.7 mg/hr for the first 18 hours and averaged 9.6 mg/hr for the final 7 hrs. This release rate was found to be identical virtually to the release rate of products made entirely of Poroplastic loaded with the same fragrance.

EXAMPLE 3

An 0.005-inch thick layer of Poroplastic material was coated onto 0.045-inch and 0.065-inch thick nonwoven cotton felt, and the laminate was impregnated with a fragrance. In the case of the thinner sample, the coating held 75 mg/in$^2$ of S5, while the 0.045 cotton felt held 764 mg/in$^2$ of S5, for a total loading of 838 mg/in$^2$ of fragrance; however, the 0.065 cotton felt held 1.604 mg/in$^2$, for a total loading of 1.679 mg/in$^2$. Under accelerated test conditions, the thinner sample released fragrance at a rate of 16.5 mg/hr, while the thicker sample released fragrance at 17.2 mg/hr, both over a period of 22 hours. In both cases, the measured release rate was in good agreement with the blotter/laminate sample of Example 2, and all previous tests on products made entirely with PLC film along illustrating that the controlled release properties of the composite material can be obtained by employing a thin membrane or overlay surface of PLC film residing on a less expensive reservoir material containing a majority of the total fragrance payload.

What we claim is:

1. A vapor-dispenser product which comprises in combination:
   (a) a reservoir means comprising a nonflowing, volatile, liquid material therein whose vapor is to be dispensed into the environment;
   (b) a cover means completely surrounding the reservoir means, at least part of which cover means comprises a thin, overlay, inert, polymeric, surface-membrane material to define a vapor-emitting surface, the overlay membrane material characterized by an ability to absorb preferentially the volatile liquid material from the reservoir and a plurality of generally uniformly distributed, open-cell-type pores through the membrane material and distributed over the vapor-emitting surface, the pores filled with liquid from the reservoir, so as to permit vaporization of the liquid from the liquid-filled pores of the surface, the liquid material within the pores of the membrane having a mobility to pass in the liquid phase through the pores of the membrane, the pore size sufficiently small to prevent leakage of nonvaporized liquid from the membrane surface and to ensure nondepletive replenishment of the liquid within the membrane from the liquid within the reservoir means; and
   (c) a thin overlay material over the vapor-emitting surface comprising a macroporous sheath material, to control the rate of evaporation of the volatile material from the reservoir, whereby the material in the reservoir means is conveyed as liquid through the pores of the surface-membrane material and vaporized from the vapor-emitting surface into the atmosphere at a controlled rate and constantly replenished by liquid from the reservoir means.

2. The product of claim 1 wherein the reservoir means comprises a nonaqueous, gel-like material containing the liquid volatile material.

3. The product of claim 1 wherein the reservoir means comprises a liquid, drainage-resistant, porous, inert, high-volumetric liquid-capacity material containing the volatile material.

4. The product of claim 3 wherein the reservoir means comprises a flexible, fibrous, web-like material which contains at least twice its dry weight of the contained liquid material.

5. The product of claim 3 wherein the reservoir means comprises an open-cell, flexible, cellular material which contains at least twice its dry weight of the contained liquid material.

6. The product of claim 1 wherein the product includes a nonvapor-permeable backing sheet material to which the thin overlay surface-membrane material is secured to confine the reservoir means, thereby providing a nonpermeable surface and a vapor-emitting surface.

7. The product of claim 6 wherein the backing sheet material comprises a nonpermeable, thermoplastic material.

8. The product of claim 1 wherein the thin overlay surface-membrane comprises a thin, thermoplastic, porous sheet material characterized by a plurality of substantially uniform pores throughout the film.

9. The product of claim 1 wherein the liquid material contains a color change indicator which changes color or intensity as the liquid vaporizes.

10. The product of claim 1 wherein the thin overlay surface-membrane material comprises a polymer-liquid composite material containing at least 70% by weight of a liquid, and having pores of less than about 250 Angstroms.

11. The product of claim 10 wherein the polymer-liquid composite material includes a heat-sealable, fibrous base material to which the polymer-liquid material is bonded, the base material having pores larger than the pores of the polymer-liquid material.

12. The product of claim 1 which includes a net-like plastic surface covering extending over the thin overlay surface-membrane material to inhibit contact of the hands of the user with the membrane surface and enhance its appearance.

13. The product of claim 1 wherein the reservoir liquid material comprises a volatile fragrance which is to be dispensed into the environment.

14. The product of claim 1 wherein the membrane material has a thickness ranging from about 5 to 15 mils in thickness.

15. The product of claim 1 wherein the membrane material has a pore size of from about $10^{-3}$ to $10^{-1}$ microns.

16. The product of claim 1 wherein the reservoir means comprises a porous, inert, polymeric, open-cell foam material.

17. The product of claim 1 wherein the reservoir means comprises a flat sheet having a thickness ranging from about 25 to 250 mils in thickness.

18. The product of claim 1 wherein the polymeric material comprises cellulose triacetate, polyethylene or polypropylene.

19. The product of claim 18 wherein the polymer-liquid material is bonded to a sheet of a nonwoven, polyethylene, porous sheet material.

20. The product of claim 19 wherein the reservoir means and the cover means both comprise overlying, flat sheet materials, and wherein the nonwoven polyethylene material, bonded to the polymeric material, is peripherally heat-sealed about the edges thereof to contain the reservoir means therein.

21. A method of dispensing a vapor into an environment, which method comprises placing in the atmosphere, into which the vapor is to be dispensed, a vapor dispenser of claim 1.

22. A vapor dispenser which comprises in combination:

(a) a reservoir means which comprises a nonflowing, volatile, liquid material therein whose vapor is to be dispensed into the environment;
(b) a vapor-nonpermeable backing sheet material;
(c) an overlay, thin, flexible, composite sheet material having a thickness of up to about 20 mils, and comprising a porous polymer-liquid sheet material containing at least 70% by weight of a liquid material, whose vapor is to be dispensed, bonded to a thin layer of porous, polymeric heat-sealable, thermoplastic material, the polymer-liquid sheet material forming a vapor-emitting surface, the pores of the polymer-liquid material being smaller in size than the pores of the heat-sealable sheet or reservoir means; and
(d) the heat-sealable material secured about its peripheral edges to the backing sheet to enclose the reservoir means in fluid-tight relationship and to provide a vapor-emittor surface, whereby the material from the reservoir is dispensed in vapor form in a controlled release from the vapor-emittor surface.

23. The vapor dispenser of claim 22 wherein the backing sheet comprises a solid, rigid, thermoplastic sheet material.

24. The vapor dispenser of claim 22 wherein the backing sheet comprises a thin, flexible, thermoplastic sheet material, and wherein the vapor dispenser is in an annular form and the material to be dispensed is a volatile fragrance.

25. The vapor dispenser of claim 22 wherein the liquid material includes a color change indicator which indicates when over about 90% of the liquid has vaporized from the reservoir.

26. The vapor dispenser of claim 22 which includes a macroporous sheath material covering the outer vapor-emitting surface of the polymer-liquid material to control evaporation of the vapor from the surface.

27. The vapor dispenser of claim 22 wherein the reservoir means comprises a gel material which includes a material whose vapor is to be dispensed, the material containing at least two times its dry weight of a liquid, which liquid includes a component whose vapor is to be dispensed.

28. The vapor dispenser of claim 22 wherein the reservoir means comprises an inert, nondraining, porous, high-liquid-volumetric-capacity material containing at least two times its dry weight of a liquid, which liquid includes a component whose vapor is to be dispensed.

29. A vapor-dispenser product which comprises in combination:
(a) a reservoir means comprising a nonflowing, volatile, liquid material therein whose vapor is to be dispensed into the environment; and
(b) a cover means completely surrounding the reservoir means, at least part of which cover means comprises a thin, overlay, inert, polymeric, surface-membrane material to define a vapor-emitting surface, wherein the surface-membrane material comprises a polymer-liquid composite material containing at least 70% by weight of the liquid material and characterized by pores of less than about 250 Angstroms, the polymer-liquid composite material bonded to a heat-sealable, porous, fibrous base material, the base material having pores larger than the pores of the polymer-liquid composite material, the overlay membrane material characterized by an ability to absorb preferentially the volatile liquid material from the reservoir and a plurality of generally uniformly distributed, open-cell-type pores through the membrane and distributed over the vapor-emitting surface, the pores filled with liquid from the reservoir, so as to permit vaporization of the liquid from the liquid-filled pores of the surface, the liquid material within the pores of the membrane having a mobility to pass in the liquid phase through the pores of the membrane, the pore size sufficiently small to prevent leakage of nonvaporized liquid from the membrane surface and to ensure nondepletive replenishment of the liquid within the membrane from the liquid within the reservoir means, whereby the material in the reservoir means is conveyed as liquid through the pores of the surface-membrane material and vaporized from the vapor-emitting surface into the atmosphere at a controlled rate and constantly replenished by liquid from the reservoir means.

* * * * *